United States Patent [19]

Marpel

[11] Patent Number: 4,796,475
[45] Date of Patent: Jan. 10, 1989

[54] PERSONAL AIR SAMPLING IMPACTOR

[75] Inventor: Virgil A. Marpel, Maple Plain, Minn.

[73] Assignee: Regents of the University of Minnesota, Minneapolis, Minn.

[21] Appl. No.: 67,106

[22] Filed: Jun. 25, 1987

[51] Int. Cl.[4] .......................... G01N 7/00; G01N 31/00; G01N 15/02; G01N 1/00
[52] U.S. Cl. ..................................... 73/863.22; 73/28; 73/8; 55/270; 422/101
[58] Field of Search .................... 422/122, 124, 83; 73/863.22, 863.23, 863.41, 863.57; 55/320, 321, 225, 332, 270

[56] References Cited

U.S. PATENT DOCUMENTS

| 3,693,457 | 9/1972 | Pilat | 55/325 |
| 3,949,594 | 4/1976 | Treaftis et al. | 55/270 |
| 3,957,469 | 5/1976 | Nebash | 55/320 |
| 3,966,439 | 6/1976 | Vennos | 55/320 |
| 4,321,822 | 3/1982 | Marple et al. | 55/270 |

FOREIGN PATENT DOCUMENTS 0427468 4/1926 Fed. Rep. of Germany ........ 55/332

Primary Examiner—Barry S. Richman
Assistant Examiner—T. J. Wallen
Attorney, Agent, or Firm—Kinney & Lange

[57] ABSTRACT

A compact air sampling impactor assembly has an inlet nozzle overlying an impaction plate that is mounted on a flat housing that defines an interior chamber covered by a filter. An air flow outlet tube leading from the chamber is connected to an air pump and a flow is established through the nozzle so the air impinges on the impaction plate to leave particles thereon and the flow then passes through the filter to the chamber and then out the air outlet. The size is kept small for personal use. Cascade impactors can be made using additional flow paths defining covers in association with the basic impactor plate and filter-carrying housing.

8 Claims, 1 Drawing Sheet

PERSONAL AIR SAMPLING IMPACTOR

BACKGROUND OF THE INVENTION

1. Field of the Invention

The present invention relates to ambient air sampling impactors that are simple and compact, and capable of being worn by a person for air sampling.

2. Description of the Prior Art

Inertial impactors used for sampling air to determine the quality of the air are well known. Impactors classify airborne particles by their aerodynamic diameter, which is the same particle property important in predicting the disposition of the particle in human airways.

The most standard design for an impactor is to have a jet of particle-laden air impinging upon an impaction plate, so that particles with high enough inertia will impact upon the plate and be separated from the air stream, and those which are small may be carried through one or more additional stages in a cascade impactor, or may be immediately passed through a filter where they are collected. If several impactor stages are used, and the particles collected at each stage are analyzed, information on the size distribution of the particles in the air is obtained. It is also a fairly common to have just a single stage impactor where the particles larger than a cutoff size are separated out, and the smaller particles are collected on a filter.

Personal air samplers are worn on the body of an individual. An air pump is also carried by the individual, for example, on a belt. These samplers are sometimes cyclones, such as the prior art Dore-Oliver Cyclone, and in some instances impactors have been used for personal sampling as well. Normally a single stage impactor followed by a filter is the most convenient because it is much lighter than a conventional cascade impactor and, of course, since the instrument is to be worn by an individual, both the weight and compactness of the instrument have to be considered.

SUMMARY OF THE INVENTION

The present invention relates to a personal air sampling impactor of a light weight and compact design, whether used as a single stage sampler or as a multistage, cascade sampler. The commonly known nozzle and impaction plate relationship is utilized with an outlet filter. The housing for the filter is made integral with the impaction plate support for lighter weight and more compactness. After the air impinges upon the impaction plate in the present invention, the air flows around the impaction plate and filter support, and the particles not collected on the impaction plate are removed in the filter on the back side of the impaction plate. The impaction plate and filter holder are in one unit, and thus it can be rather thin in relation to its diameter or cross-dimension, lending itself easily to personal impactor use.

A ring supports the housing which holds the impaction plate and filter. The ring forms an outer housing covered with end caps that are held frictionally in place with O-rings and which can be removed for servicing. The air is drawn out of the outer housing to provide the necessary flow through the sampler. Normally the pump for providing the air flow is supported by the individual and can be driven with power from a battery pack.

The cascade impactors shown as variations of the present invention also use the basic configuration impaction plate and filter and have additional plates supported so that the size is reduced and the air flow path reverses direction.

DETAILED DESCRIPTION OF THE PREFERRED EMBODIMENTS

Figure 1:
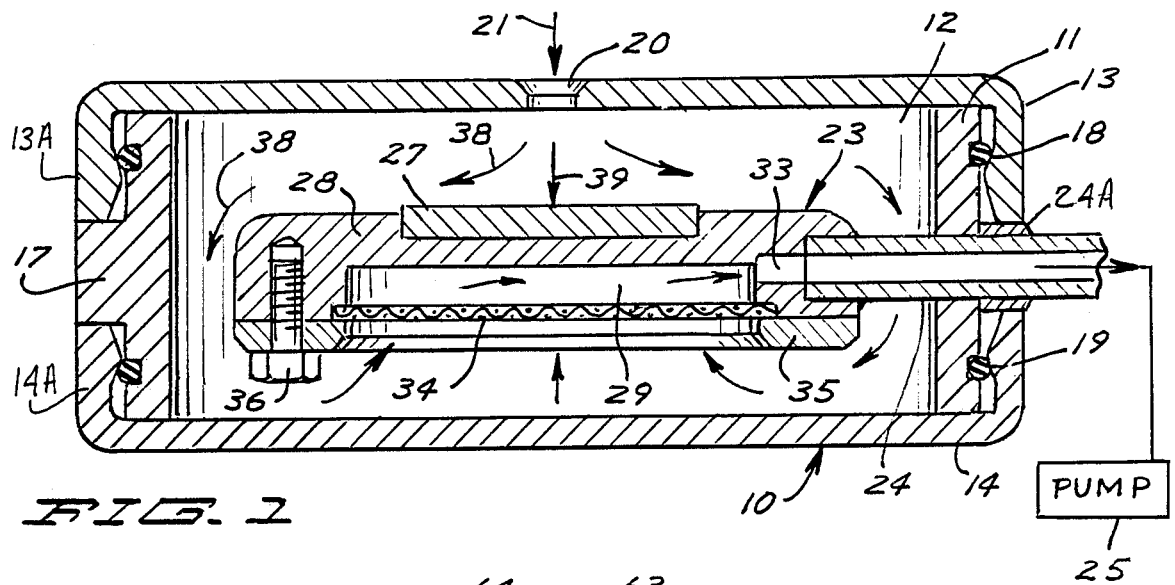
FIG. 1 is a sectional view through a personal sampling impactor made according to the present invention.

In FIG. 1, a personal sampling impactor assembly, indicated generally at 10, comprises a housing ring 11 that is annular as shown, and which can be of relatively small size. The ring 11 defines an interior chamber 12. The ring is covered with a first front cover 13 and a second rear cover 14 that have annular side flanges or walls 13A and 14A surrounding the ring 11 and which are held in place against an annular central rim 17 on the ring 11. Suitable O-rings 18 and 19 are provided on the exterior of ring 11, and retain the covers 13 and 14 in place. The cover walls 13A and 14A have annular lips or ribs that ride over the O-rings and snap in place to hold the covers. The covers can be removed by using a coin or small pry to lift the covers from the rim 17. Each of the covers 13 and 14 can have a slot at the edge of its respective wall 13A and 14A for inserting the coin for twisting to remove the covers if desired.

The cover 13 has an end wall with an inlet orifice or nozzle 20 through which air flow indicated by the arrows 21 can pass. An impactor plate assembly indicated generally at 23 made according to the present invention is supported on the interior chamber 12 through the use of a rigid flow tube 24 that is fixed to the ring 11 and the rim 17 thereof with a ferrule 24A. The flow tube extends out from ring 11 a desired amount. The outer end of tube 24 is connected to a suitable air pump 25. The pump can be supported on a person carrying the impactor.

The impaction plate assembly 23 includes an impaction plate 27 that is supported in a plate housing 28. The housing 28 is circular in plan view (or it could be other outer configurations if desired), and has an internal cavity indicated at 29 formed therein on an opposite side from the impaction plate 27. The housing 28 is relatively flat and is smaller in diameter than ring 11. The flow tube 24 opens through a passageway 33 to the cavity 29. The outer opening to the cavity 29 is covered with a filter 34 that is held in place with a suitable ring 35 that can be fastened with set screws 36 to the housing 28.

The orifice or nozzle 20 is selected in size for the flow desired and, once the pump 25 is operated, the flow indicated by arrows 21 will enter through the nozzle 20 and will impinge upon the impaction plate 27 as indicated by the arrows 39 and, of course, the flow will also diverge as indicated by the arrows 38 and will pass around the housing 28 within the chamber 12 and change direction to pass through the filter 34 and then out through the tube 24 to the pump 25.

The front and rear covers 13 and 14 are nearly identical in design, except that the front cover 13 has nozzle or orifice 20 formed in it. Both covers snap into place over the O-rings 18 and 19 so that they are tightly held, and sealed, but yet are removable. The front cover is removed for cleaning the impaction plate 27, and the rear cover 14 is removed to remove the filter and the filter holder.

The parts, that is, the housing 28, ring 11 and covers 13 and 14 can be made of metal, or can be a suitable plastic. The cutoff size of the particles carried around and through filter 34 is selected in a normal manner. When done sampling air, the particles collected on the filter can be analyzed, as can the particles collected by impaction plate 27.

Figure 2:
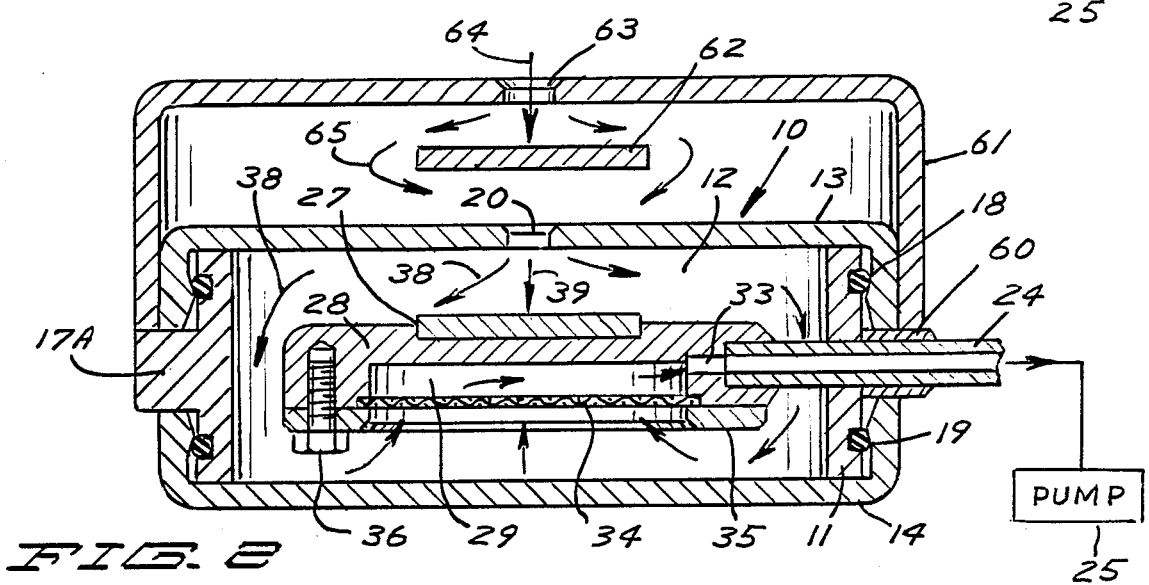
FIG. 2 is a sectional view showing an additional impactor stage added to the personal sampling impactor of FIG. 1.

A modified form of the invention is shown in FIG. 2, wherein the personal sampling device 10 is substantially identically constructed, but it is made into a cascade impactor by adding an additional cover having an inlet orifice or nozzle. The only change that needs to be made (in the impactor device 10) for the cascade impactor of FIG. 2 is that the rim 17 is radially extended as shown at 17A, and the ferrule or sleeve shown at 60 to support the flow tube 24 is extended.

A cup shaped outer cover 61 is placed over the front cover 13 and can be held in place with friction fittings or with a screw or even with an O-ring, as shown for holding covers 13 and 14 in place, and the cover 61 carries an impaction plate 62 fixed to the interior thereof. The impaction plate 62 is supported on the cover in a desired manner, and spans across the cover 61 (from one side to the other), so that it aligns with the inlet orifice 20. The cover 61 has an inlet orifice or nozzle 63 defined therein that is a selected larger size then the orifice 20, and which is aligned with an impaction plate 62, so that incoming air impinges on the impaction plate 62 after it flows through the orifice 63, as shown by the arrows 64. The air will then flow around the impaction plate 62 as shown by the arrows 65 and enter the orifice 20. The subsequent flow is then as described in relation to FIG. 1 and is shown by the arrows 38, up through the filter 34 and out the flow tube 24 to the pump 25. Two stage cascade impaction thus is achieved in a very compact unit. The axial height (perpendicular to the plane of the impaction plates) is substantially less than the diameter of the housings.

Figure 3:
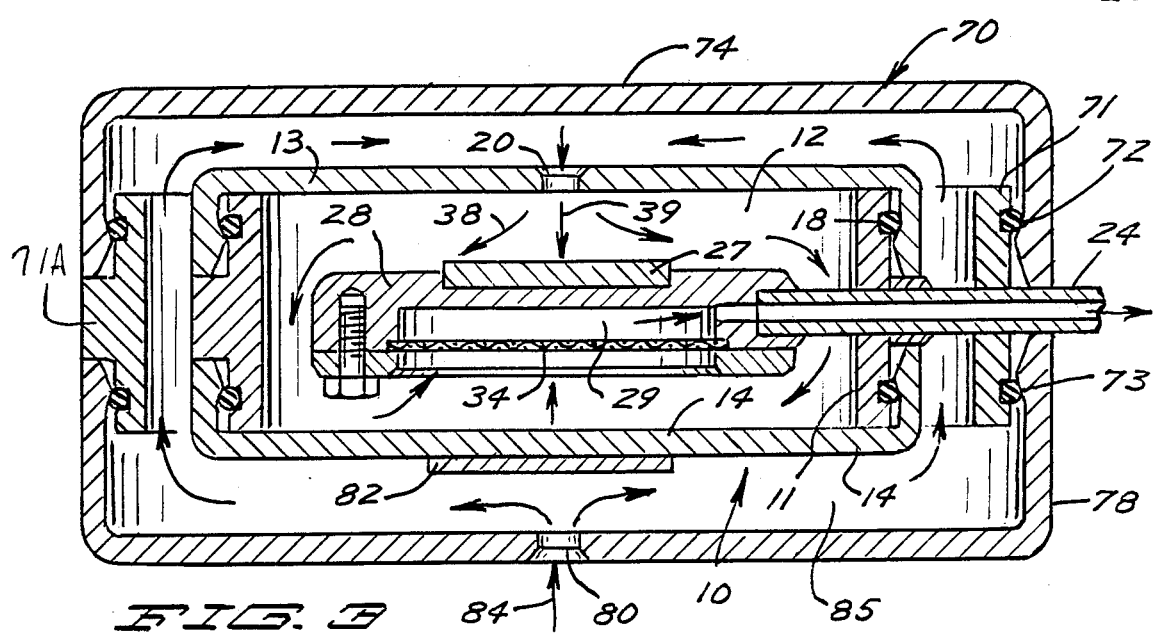
FIG. 3 is a further modified form of the invention showing a different type of a cascade impactor utilizing the device shown in FIG. 1 in an outer housing.

In FIG. 3, a further modified form of the invention is shown, and comprises a cascade personal impactor 70. The impactor 10 is mounted in impactor 70 and is again identically constructed to the first form of the invention, and bears like numbers. The cascade impactor 70 comprises a second outer ring 71 that surrounds the personal impactor 10 of the first form of the invention, and the ring 71 is mounted onto an outwardly extending portion of the flow tube 24 to be held in place concentric with the personal impactor 10. The flow tube 24 can be inserted in any desired manner, or could be placed through a slot in the ring 71 and clamped in place. The ring 71 also has an annular rim 71A.

The ring 71 carries O-rings 72 and 73 on its outer periphery. An outer cup-shaped cover 74 is snapped over the ring 71 and retained in place with the O-ring 72. The cover 74 has a small internal rib adjacent its outer edges, so that they are held sealed and retained in place. The cover 74 is a cup shaped cover that is totally closed.

A second cover 78 is also cup shaped, and fits over the ring 71 and is held in place with the O-ring 73. The end wall of cover 78 has an inlet orifice or nozzle 80 therein, which aligns with an impaction plate 82 that is mounted on the outer surface of the rear cover 14 of the personal sampling impactor 10. The impaction plate 82 is aligned with the orifice 80, and air inflow through orifice 80 as shown by the arrow 84 will impinge against the impaction plate 82 to cause separation of particles. The orifice 80 is of larger size than the orifice 20. The air flows through the interior chamber 85 that is formed by the covers 74 and 78 and the ring 71. The air flows between the inner periphery of ring 71 and the outer periphery of the personal impactor 10, and then flows into the orifice 20 where it impinges against impaction plate 27 as previously shown and explained. The flow goes through the filter 34 and flow tube 24 to a pump such as pump 25.

There can be multiple nozzles or orifices instead of the single inlet nozzles shown. The nozzles or orifices can be rectangular instead of round, or if a higher flow rate is desired, the impactor can be somewhat larger.

The unit is generally pancake shaped. Because the basic personal impactor 10 has the filter and housing for supporting the impactor plate as one unit, with an interior chamber that provides for air flow through a rigid flow tube, the size is kept small. The flow chambers are formed with a generally flat ring that surrounds the interior housing. The assembly is small sized and very convenient to wear because it is light weight. Even the cascade type devices retain compactness, a generally "pancake" form, and they maintain a light construction. The covers that are shown can be snapped off as desired for cleaning and servicing, and the covers are easily made. The design is enclosed, and thus the particles are collected with very few losses, which is desirable.

Of course, additional housings can be used over the form shown in FIG. 3, to have further cascade type impactor features.

Although the present invention has been described with reference to preferred embodiments, workers skilled in the art will recognize that changes may be made in form and detail without departing from the spirit and scope of the invention.

What is claimed is:

1. An impactor comprising an impaction plate and filter unit including an impactor housing having oppositely facing first and second sides bounded by an outer wall, said impactor housing having an exterior surface on the first side thereof, an impaction plate mounted on said exterior surface of said impactor housing, a chamber defined by a recess in said impactor housing which opens to the second side of the impactor housing and which faces in opposite direction from said impaction plate, filter means for covering said opening, means defining an air outlet from said chamber for connection to an air flow producing means for creating an air flow through said air outlet and through said opening, and outer housing means supported relative to and surrounding said impactor housing and defining a second chamber around said impactor housing, said outer housing means having an inlet nozzle opening therethrough aligned with said impaction plate so that when flow is created through said air outlet, air flows inwardly through the nozzle of the outer housing means and impinges against the impaction plate and flows around said impaction plate to reverse flow direction and flow through said filter and out through said air outlet.

2. The apparatus as specified in claim 1 and an outer cover positioned around at least a portion of the outer housing means, said outer cover having a second nozzle therein, a second impactor plate aligned with the second nozzle, said outer cover defining a chamber in cooperation with the outer housing that is open to said first mentioned nozzle.

3. The apparatus as specified in claim 1 wherein said outer housing means comprises a ring surrounding said impactor housing, said outer housing further comprising a pair of covers mounted on said ring and sealingly held in place thereon to define a chamber that surrounds the impactor housing.

4. The apparatus of claim 1 wherein said air outlet comprises a conduit fixed to said impactor housing and extending laterally therefrom.

5. The apparatus of claim 4 and a ring member supported on the rigid conduit and spaced from and surrounding the outer housing; cover means enclosing said ring member, said cover means having a cover wall enclosing the inlet nozzle, the cover means having a second inlet nozzle therein, a second impactor plate aligned with said second inlet nozzle, said cover means and ring defining a flow path from the second inlet nozzle to said first inlet nozzle.

6. A personal air sampling impactor comprising an impaction plate and filter unit including an impactor housing having an outer periphery and a thickness and oppositely facing first and second surfaces bounded by the outer periphery, the first surface defining a plane and being parallel to a central plane of the impactor housing, an impaction plate mounted on the first surface on the exterior of said impactor housing and facing in a first direction, a chamber defined in said impactor housing and formed by a recess in the impactor housing opening to the second surface of the impactor housing and facing in a second direction opposite from the first direction, filter means for covering said opening to said chamber, means defining an air outlet from said chamber for carrying an air flow through said air outlet and through said opening comprising a passageway formed in the impactor housing and extending from the chamber, a conduit fixed to the impactor housing and extending outwardly from the outer periphery generally parallel to the central plane, and outer housing means surrounding said impactor housing and defining a second chamber therearound, said outer housing having an inlet nozzle opening therethrough aligned with said impaction plate so that when flow is created through said air outlet air flows inwardly through the nozzle and impinges against the impaction plate and flows through said filter out through said air outlet, the conduit being fixed to the outer housing means and forming the support for the impactor housing.

7. The apparatus as specified in claim 6 and an outer cover positioned around at least a portion of the outer housing means, said outer cover having a second nozzle therein, a second impactor plate aligned with the second nozzle, said outer cover defining a chamber in cooperation with the outer housing that is open to said first mentioned nozzle.

8. The apparatus as specified in claim 6 wherein said outer housing means comprises a ring surrounding said impactor housing, said outer housing further comprising a pair of covers mounted on said ring and sealingly held in place thereon to define a chamber that surrounds the impactor housing.

* * * * *

UNITED STATES PATENT AND TRADEMARK OFFICE
CERTIFICATE OF CORRECTION

PATENT NO. : 4,796,475
DATED : January 10, 1989
INVENTOR(S) : Virgil A. Marple

It is certified that error appears in the above-identified patent and that said Letters Patent is hereby corrected as shown below:

On the first page of the patent, in the line marked "75", please replace the inventor with the correct spelling of:
-- 75 Inventor: Virgil A. Marple, replacing Virgil A. Marpel
-- 19 "Marpel" should read --Marple--.

Signed and Sealed this

Twenty-fifth Day of July, 1989

Attest:

DONALD J. QUIGG

Attesting Officer

Commissioner of Patents and Trademarks